US008870764B2

(12) United States Patent
Rubin (10) Patent No.: US 8,870,764 B2
(45) Date of Patent: Oct. 28, 2014

(54) MULTI-MODAL SLEEP SYSTEM

(75) Inventor: Benjamin Rubin, Boston, MA (US)

(73) Assignee: ResMed Sensor Technologies Limited (IE)

( * ) Notice: Subject to any disclaimer, the term of this patent is extended or adjusted under 35 U.S.C. 154(b) by 35 days.

(21) Appl. No.: 13/226,121

(22) Filed: Sep. 6, 2011

(65) Prior Publication Data

US 2013/0060097 A1 Mar. 7, 2013

(51) Int. Cl.
*A61B 5/00* (2006.01)
*A61B 5/0476* (2006.01)
*A61B 5/11* (2006.01)

(52) U.S. Cl.
CPC ............. *A61B 5/0476* (2013.01); *A61B 5/0006* (2013.01); *A61B 5/4812* (2013.01); *A61B 2562/0219* (2013.01); *A61B 5/1118* (2013.01); *A61B 5/6803* (2013.01); *A61B 2560/0412* (2013.01); *A61B 2560/0468* (2013.01)
USPC ......................................................... 600/301

(58) Field of Classification Search
USPC .................................................. 600/300–301
See application file for complete search history.

(56) References Cited

U.S. PATENT DOCUMENTS

| | | | | |
|---|---|---|---|---|
| 5,047,930 | A * | 9/1991 | Martens et al. ................ | 600/301 |
| 6,120,441 | A * | 9/2000 | Griebel .......................... | 600/300 |
| 6,306,088 | B1 * | 10/2001 | Krausman et al. ............ | 600/301 |
| 6,625,485 | B2 * | 9/2003 | Levendowski et al. ....... | 600/544 |
| 7,542,803 | B2 * | 6/2009 | Heruth et al. .................. | 607/46 |
| 2005/0042589 | A1 * | 2/2005 | Hatlestad et al. ............. | 434/262 |
| 2007/0010722 | A1 * | 1/2007 | Suzuki et al. ................. | 600/300 |
| 2007/0197878 | A1 * | 8/2007 | Shklarski ....................... | 600/300 |
| 2007/0249952 | A1 | 10/2007 | Rubin et al. | |
| 2008/0009685 | A1 * | 1/2008 | Kim et al. ...................... | 600/300 |
| 2008/0064934 | A1 * | 3/2008 | Frei et al. ....................... | 600/300 |
| 2008/0319277 | A1 * | 12/2008 | Bradley ......................... | 600/301 |
| 2009/0275805 | A1 * | 11/2009 | Lane et al. ..................... | 600/300 |
| 2009/0318782 | A1 * | 12/2009 | Fernandez et al. ............ | 600/301 |
| 2010/0049008 | A1 * | 2/2010 | Doherty et al. ................ | 600/301 |
| 2010/0099954 | A1 | 4/2010 | Dickinson et al. | |

(Continued)

OTHER PUBLICATIONS

"Automatic Sleep Stage Scoring System Using Genetic Algorithms and Neural Network," Engineering in Medicient and Biology Society, 2000, Proceedings of the 22nd Annual Internation Coverence of the IEEE, 2000.

(Continued)

*Primary Examiner* — William Thomson
*Assistant Examiner* — Bobby Soriano
(74) *Attorney, Agent, or Firm* — Lerner, David, Littenberg, Krumholz & Mentlik, LLP (57) ABSTRACT

Systems and methods are provided for a multi-modal sleep system comprising a data processor for operating in a plurality of operating modes. The data processor may detect at least one sensor providing data to the data processor and determine a sensor type associated with each of the at least one sensor. The data processor may select a mode of operation based on the determined sensor type of the detected at least one sensor and of each of the at least one sensor. A first of the plurality of operating modes may be selected in response to determining that the at least one detected sensor includes a first sensor type or combination of sensor types. The data processor may be configured to receive data from the at least one detected sensor and process the received data according to the selected mode of operation to output a characterization of a user's sleep.

26 Claims, 5 Drawing Sheets

(56) References Cited

U.S. PATENT DOCUMENTS

| | | | |
|---|---|---|---|
| 2010/0198289 A1* | 8/2010 | Kameli et al. | 607/14 |
| 2011/0015495 A1* | 1/2011 | Dothie et al. | 600/300 |
| 2011/0092831 A1* | 4/2011 | Herscovici-Cohen et al. | 600/500 |
| 2011/0178377 A1* | 7/2011 | Heneghan et al. | 600/301 |
| 2011/0190599 A1* | 8/2011 | Wang et al. | 600/301 |
| 2011/0251469 A1* | 10/2011 | Varadan | 600/301 |
| 2011/0306850 A1* | 12/2011 | Hatlestad et al. | 600/301 |
| 2012/0029301 A1* | 2/2012 | Battista, Jr. | 600/300 |
| 2012/0029322 A1* | 2/2012 | Wartena et al. | 600/301 |
| 2013/0012785 A1* | 1/2013 | Lombardi et al. | 600/301 |

OTHER PUBLICATIONS

Stephen W. and Jennifer R. Spiro, "Comparing Different Methodologies Used in Wrist Actigraphy", Sleep Review, Summer 2001, available at http://www.sleepreviewmag.com/issues/articles/2001-07-04.asp.

* cited by examiner

MULTI-MODAL SLEEP SYSTEM

FIELD OF THE INVENTION

This application relates to a multi-modal sleep system operable in one of several modes.

BACKGROUND OF THE INVENTION

There are various sleep devices in the market today. Some sleep devices are used in sleep labs for diagnosing sleep-related illnesses or conditions. In those applications, the sleep devices employ wet electrodes for detecting signals such as EEG (Electroencephalography), EMG (Electromyography), and EOG (Electrooculargraph), signals of a user for diagnostics. The application of wet electrodes to skin generally requires a conductive gel on the electrode to secure the attachment of the electrode to skin. These wet electrode based systems are thought to be uncomfortable and not suitable for home use, despite the fact that some wet electrodes provide better EEG signal recordings than certain other competing electrodes. In the consumer market, there are now take-home sleep devices that allow a user to monitor and/or track sleep at home. Many of these take-home sleep devices utilize accelerometers to track the physical movements of a user while asleep, e.g., the tossing and turning experienced by the user. Also available now in the consumer market is a sleep tracking device offered by Zeo Inc., which employs dry electrodes, as opposed to wet electrodes, for sensing EEG signals of a user while asleep. The application of dry electrodes to a user's skin requires a headband to secure the dry electrodes to skin.

However, the above-described sleep devices are single mode devices as each device relies on a single mechanism for receiving input signals (e.g., wet electrode, accelerometer, or dry electrode). Additionally, users prefer more choices in terms of the different ways of wearing or using a sleep device. For example, a user may prefer wearing a headband on some nights and a wristband on other nights. These single-mode devices in the market today limit a user to only one form of use (e.g., wearing a wristband, wearing a headband, etc.). While some sleep analysis devices include multiple sensor modalities, for example a combination of EEG electrodes and an accelerometer, such devices are not capable of determining which sensor modalities are actually outputting usable data and adjusting their operation accordingly. Thus, there exists a first need in the art for a multi-modal sleep device capable of adjusting its mode of operating based on a determination of which of a plurality of sensors is outputting useful data, thereby providing users flexibility in the way in which they use the device.

SUMMARY OF THE INVENTION

In one aspect, systems and methods are provided for a multi-modal sleep system comprising a data processor. In some embodiments, the data processor is configured to operate in a plurality of operating modes. The data processor may detect at least one sensor providing data to the data processor and determine a sensor type associated with each of the at least one sensor. The data processor may select a mode of operation based on the determined sensor type of the detected at least one sensor. A first of the plurality of operating modes may be selected in response to determining that the at least one detected sensor includes a first sensor type or combination of sensor types. A second of the plurality of operating modes may be selected in response to determining that the at least one detected sensor includes a second sensor type or combination of sensor types. The data processor may be configured to receive data from the at least one detected sensor. The data processor may process the received data according to the selected mode of operation to output a characterization of a user's sleep.

In certain embodiments, the data processor is configured to select the first of the plurality of operating modes in response to detecting a single sensor including an accelerometer. The data processor may be configured to select the second of the plurality of operating modes in response to detecting a single sensor including an EEG electrode. In other embodiments, the data processor is configured to select the first of the plurality of operating modes in response to the data processor detecting a single sensor including an accelerometer.

The data processor may be configured to select the second of the plurality of operating modes in response to the data processor detecting at least two sensors including an accelerometer and at least a sensor of a second sensor type. The second sensor type may comprise a wet EEG electrode or a dry EEG electrode. The second of the plurality of operating modes may comprise an operating mode that collectively processes data output by the accelerometer and the at least one sensor of a second sensor type. The second of the plurality of operating modes may process data output by the accelerometer to weight a sleep condition analysis otherwise executed on data output by the sensor of the second type.

The data processor may be configured to select the first of the plurality of operating modes in response to the data processor detecting a sensor including a dry EEG electrode. The data processor may be configured to select the second of the plurality of operating modes in response to the data processor detecting a sensor including a wet EEG electrode.

In some embodiments, the multi-modal sleep monitoring system includes a built-in accelerometer. The condition of the user's sleep output by the data processor may indicate whether the user is awake or asleep based on data output by the accelerometer.

In certain embodiments, the multi-modal sleep monitoring system comprises a removable adapter for coupling the data processor to a sensor of a first type. In other embodiments, the data processor may be configured to couple directly to a sensor of a second type without the adapter.

The multi-modal sleep monitoring system may comprise a remote computing device configured for wireless communication with the data processor for receiving data indicative of the output sleep condition. The remote computing device may be configured for presenting sleep condition data based on the data received from the data processor.

According to another aspect, the invention relates to a method of for operating a multi-modal sleep monitoring system in a plurality of modes. The method includes a data processor detecting at least one sensor providing data to the data processor and determining a sensor type associated with each of the at least one sensor. The data processor then selects a mode of operation based on the determined sensor type of the detected at least one sensor and of each of the at least one sensor. A first of the plurality of operating modes may be selected in response to determining that the at least one detected sensor includes a first sensor type or combination of sensor types. A second of the plurality of operating modes may be selected in response to determining that the at least one detected sensor includes a second sensor type or combination of sensor types. The data processor then receives data from the at least one detected sensor and processes the received data according to the selected mode of operation to output a characterization of a user's sleep.

BRIEF DESCRIPTION OF THE DRAWINGS

The foregoing and other objects and advantages of the invention will be appreciated more fully from the following further description thereof, with reference to the accompanying drawings wherein.

DESCRIPTION OF CERTAIN ILLUSTRATED EMBODIMENTS

To provide an overall understanding of the invention, certain illustrative embodiments will now be described. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

Figure 1:
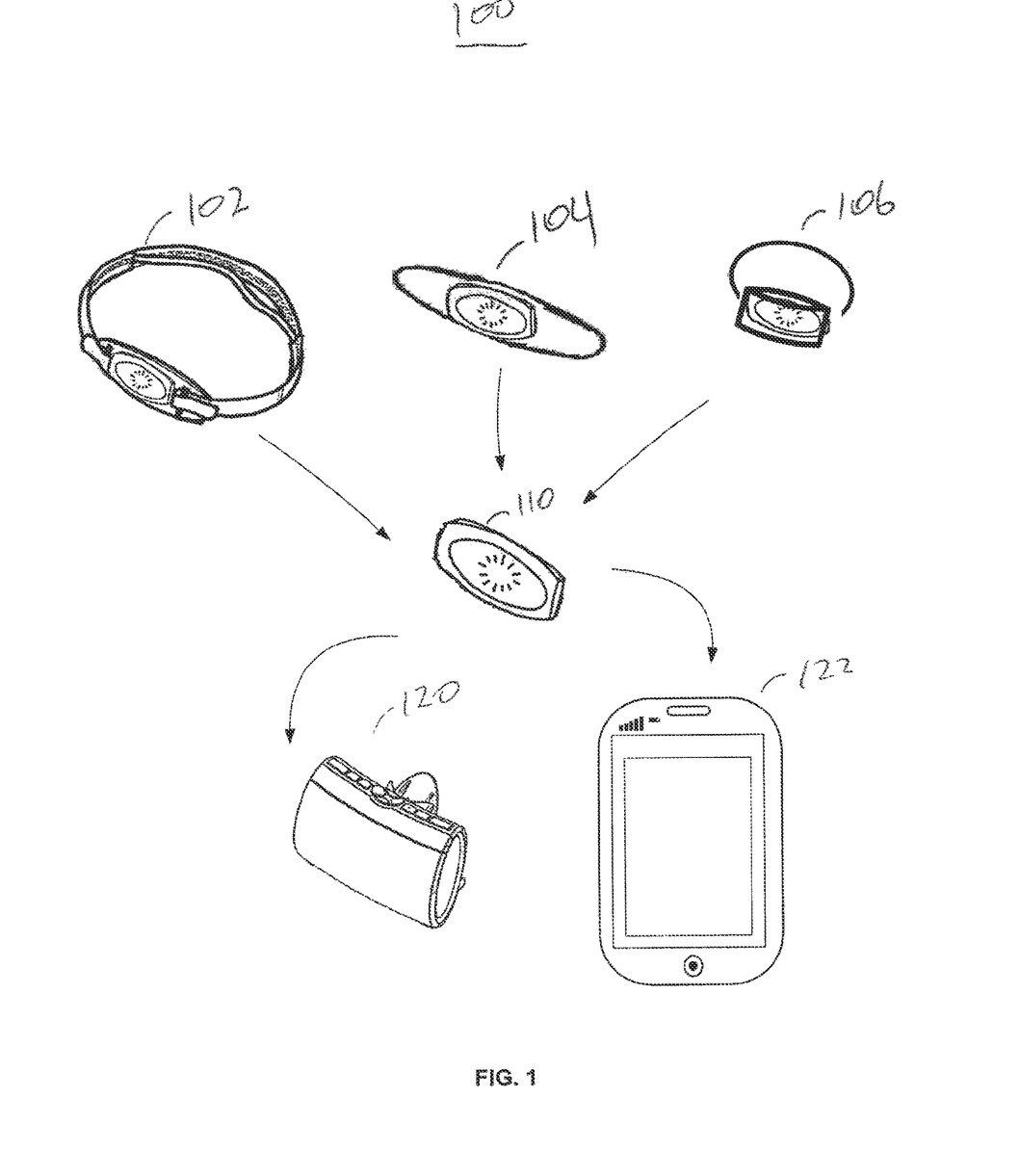
FIG. 1 depicts a multi-modal sleep system, according to an illustrative embodiment of the invention.

FIG. 1 depicts a multi-model sleep system 100, according to an illustrative embodiment of the invention. The multi-model sleep system 100 includes three modes of operation. In each mode, the system 100 includes a processing component 110 and a user interface device (such as a sleep base station 120 and a mobile device 122). The three modes of operation include a first mode of operation 102, a second mode of operation 104, and a third mode of operation 106.

In the first mode 102, the system 100 operates using a built-in accelerometer and flexible dry conductive electrodes or wet electrodes designed to be in contact with the skin of a user in the forehead region. In the second mode 104, the system 100 operates using a built-in accelerometer and wet or dry conductive electrodes also made to be in direct contact with the skin of a user in the forehead region. In the third mode 106, the system 100 uses only a built-in accelerometer for detecting physical movements of a user while asleep. In the third mode 106, the system 100 may be secured onto the wrist. Details of how the sleep system 100 is configured and operates in each of the three illustrative modes of operation are described in relation to FIGS. 2-4.

In operation, the processing component 110 receives either a raw electrical signal from the electrodes signals or movement data, or both, depending on the mode of operation. The raw electrical signal includes information indicative of one or more of EEG, muscle tone, eye movement and galvanic skin response. The processing component 110 then processes the received data, also based on the mode of operation. Based on the received data monitored during a night of sleep, the processing component 110 determines the various sleep stages that the user experienced and the duration associated with each stage. In one embodiment, sleep is classified according to the R&K standard (defined in 1968 Allan Rechtschaffen and Anthony Kales), which includes sleep stages 1, 2, 3, 4, and REM sleep as well as an awake stage. Alternatively sleep stages may be defined according to other standards, such as the standard specified by the American Academy of Sleep Medicine, which includes wake, N1, N2, N3, and REM sleep stages. In yet another alternative, the processing component 110 classifies a user's sleep into one of wake, REM, light, and deep sleep stages. The determination of sleep stages may be based on an analysis of the electrical signal received through the electrodes by itself or in conjunction with data out put by the accelerometer. In certain embodiments, other sensor modalities are incorporated into the sleep stage classification analysis in addition or in the alternative to the EEG and acceleration data. For example, in one embodiment, in addition or in the alternative to the processing component 110 including wet or dry electrodes, the processing component includes a LED/photodiode pair for generating a photoplethysmogrphic signal. This signal can be used to determine heart rate, heart rate variability, and respiration rate, one or more of which is then processed to determine sleep stages of a user.

In some embodiments, the processing component 110 performs various signal processing operations on the received signal, such as to increase the signal to noise ratio (SNR), to compute a mathematical transform of the signal for further data manipulation and information extraction, and to amplify the raw input signal. In some embodiments, processing component 110 is stored with instructions corresponding to different sets of data analysis methods for the different modes of operations. In particular, as described in relation to FIG. 2, the combination of an EEG signal and movement data indicative of a user's physical movements while asleep require a special set of analysis.

In some implementations, after the raw input signal is processed, the processing component 110 wirelessly communicates the processed data to the base station 120 or the mobile device 122. In addition to communicating wirelessly, the base station 120 and/or the mobile device 122 can be physically connected to the processing component 110 via various mechanisms. For example, the base station 120 and/or the mobile device 122 may include adapters, such as an electrically conductive holder, to enable a direct electrical contact between the processing component 110 and the base station 120 and/or the mobile device 122. In some embodiments, the processing component 110 may include an SD card, mini-SD card, micro-SD card or other suitable removable integrated circuit memory device for storing the processed data. The removable memory device can then be removed from the processing device and directly inserted into various devices, such as the base station 120, the mobile device 122, a computer, a tablet, a television, and/or any other type of device with processing and/or storage capabilities. Alternatively, or additionally, the processing component 110 can wirelessly communicate with one of the above-mentioned devices according, for example, to the BLUETOOTH, ZIGBEE, or WIFI protocols. In yet another embodiment, the data received from the processing component 110 can be forwarded to a remote server via a wired or wireless Internet connection. In some embodiments, the receiving device can perform post-processing on data collected and/or determined by the processing component 110.

In some embodiments, the base station 120 and the mobile device 122 depict the data processed by the processing component 110 in a user-readable format to a user. For example, the various sleep stages and the duration of each may be presented to the user via the base station 120 or the mobile device 122. The sleep stages may be plotted on a time-scale and displayed to the user on a screen of the base station 120 or via an application on the mobile device 122. In some implementations, the base station 120 or an application installed on the mobile device 122 can carry out a portion of the analysis of the raw input signal for the processing component 110. In other implementations, the processing component 110 offloads the entire data analysis process to the base station 120 or an application on the mobile device 122. In particular, the various data processing or analysis techniques described in co-pending U.S. patent application Ser. No. 11/586,196 ("'196 application") may be used in the wet electrode system 104 and are suitable to be used in conjunction with the processing of movement data generated by the accelerometer when both electrodes and accelerometer are used. The entirety of the '196 application is incorporated herein by reference.

In some embodiments, the base station 120 and/or the mobile device 122 are connected to the internet. Each user of the system 100 may be given a web account allowing the user to store the sleep data in a remote location accessible by a web server. The stored data may further be processed or analyzed by any tools provided to the user by a web application associated with the user account. Examples of such web based tools or applications are described in relation to co-pending U.S. patent application Ser. No. 12/387,730, the entirety of which is incorporated herein by reference.

Figure 2:
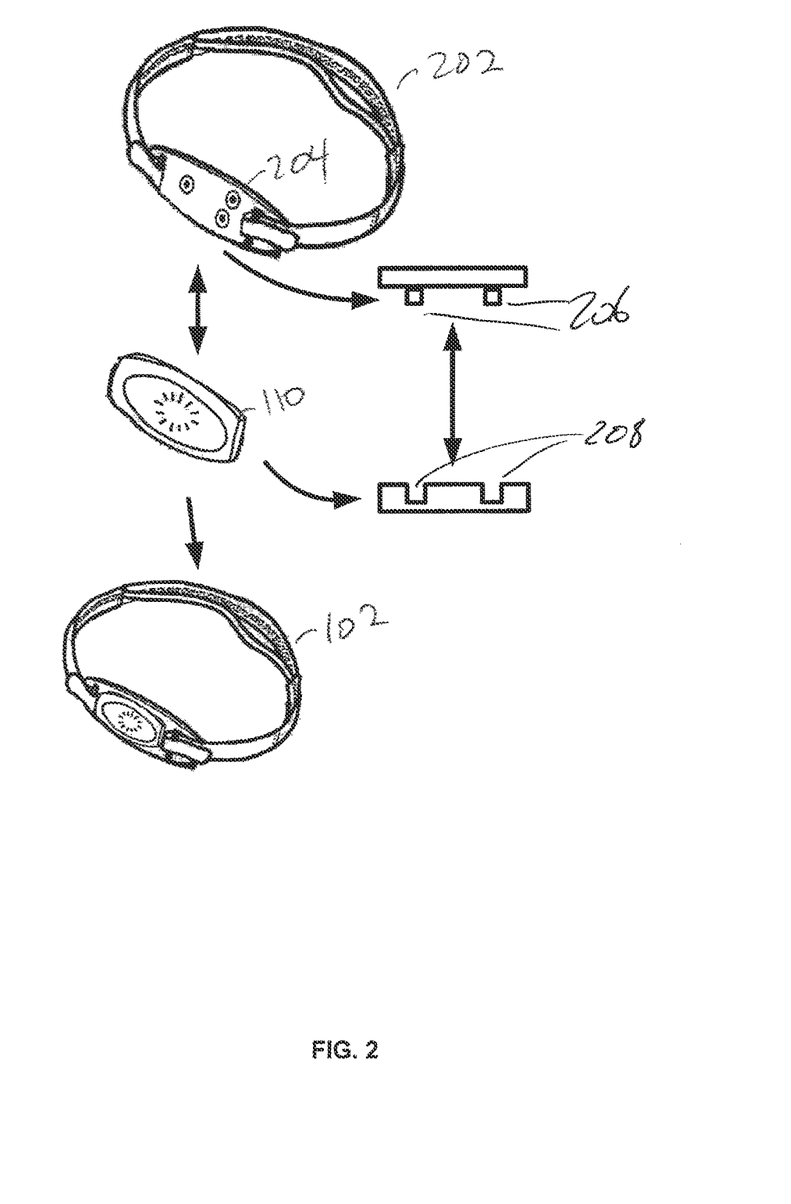
FIG. 2 depicts the multi-modal sleep system of FIG. 1 operating in a first mode of operation, according to an illustrative embodiment of the invention.

FIG. 2 depicts the multi-modal sleep system 100 of FIG. 1 operating in a first mode of operation 102, according to an illustrative embodiment of the invention. In the first mode 102, the multi-modal sleep system 100 includes a headband 202, dry electrodes 204, and the processing component 110, which has an accelerometer. In some embodiments, the headband 202, dry electrodes 204, and processing component 110 are modular and may be assembled according to the diagram illustrated in FIG. 2. In the illustrative embodiment depicted in FIG. 2, the dry electrodes 204 couple to the processing component 110 via three conductive mechanical fasteners. The male portions 206 of the mechanical fasteners extend from the dry electrodes, with corresponding female portions 208 of the fasteners built into the rear-facing side of the processing component 110. In operation, the processing component 110 receives and processes both the EEG signal sensed by the dry electrodes 204 as well as the movement data generated by the accelerometer.

In some embodiments, the processing of the EEG signal and the movement data are separate and modular. In other embodiments, the processing of the two sets of data is intertwined in that one set of data may be used to adjust the other set. For example, the movement data may be fed as input to the processing of the EEG signal, or vice versa. For instance, the processing component 110 may determine that a user is in REM sleep from 2 a.m. to 5 a.m. based on the EEG signal received during that time period. The movement data collected during the same time period may indicate a higher confidence in this assessment if the movement data indicates less tossing and turning during the same time period. Alternatively, the movement data may indicate a lower confidence in the assessment determined based on the processing of the EEG signal. In certain embodiments, the movement data may be interjected into the processing of the EEG signal before an assessment or a conclusion based on the EEG signal is determined.

In one particular example, the processing component 110 includes a neural network that outputs for each sleep time interval a score indicative of the likelihood that the user is in each stage of sleep the processing component 110 considers. The processing component then classifies the sleep time interval the sleep stage having the highest score. In one implementation, initial scores are calculated solely based on EEG data. Then, based on movement data obtained from the accelerometer, one or more of the scores may be increased or decreased prior to a final classification of the sleep time interval. For example, if the processing component detects relatively frequent movements during a time interval, the scores for the light sleep and/or wake stages may be increased or the scores for deep and/or REM sleep may be decreased. In alternative implementations, acceleration day may be used to alter the initial scoring algorithm.

Details of how an EEG signal detected by dry electrodes may be processed to determine sleep data, e.g., sleep stages, are further described in co-pending U.S. patent application Ser. No. 11/586,196, the entirety of which is incorporated herein by reference. An additional example of an EEG-based sleep staging algorithm suitable for use with the above-described system includes the algorithm disclosed in "Automatic Sleep Stage Scoring System Using Genetic Algorithms and Neural Network," Engineering in Medicient and Biology Society, 2000, Proceedings of the $22^{nd}$ Annual Internation Coverence of the IEEE, 2000. Details of how an EEG signal detected by dry, wet, or any other forms of electrodes may be processed in conjunction with movement data as detected by an accelerometer are discussed below in relation to FIG. 4.

Figure 3:
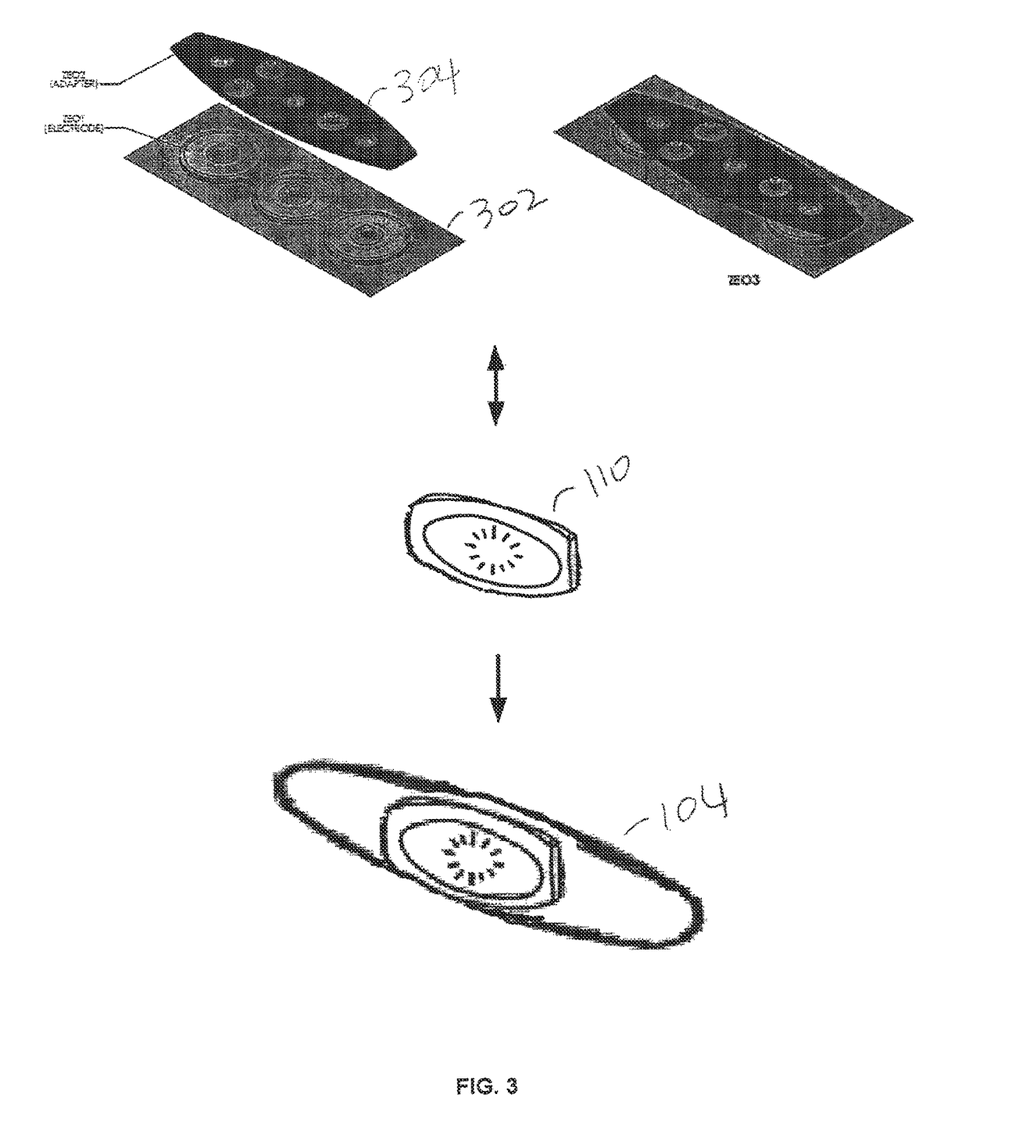
FIG. 3 depicts the multi-modal sleep system of FIG. 1 operating in a second mode of operation, according to an illustrative embodiment of the invention.

FIG. 3 depicts the multi-modal sleep system 100 of FIG. 1 operating in a second mode of operation 104, according to an illustrative embodiment of the invention. In the second mode 104, the multi-modal sleep system 100 includes wet electrodes 302, an adapter 304, and a processing component 110. The processing methods used in connection with the wet electrodes conform substantially to the processing methods used in connection with the dry electrodes as described above.

The wet electrodes 302 may include any wet electrodes. The wet electrodes 302 may be applied directly to the skin near the forehead region of a user if direct contact can be made between the wet electrodes 302 and skin. The application of the wet electrodes 302 may include the use of gel, adhesives, or any other forms of attachment. In some embodiments, to further support the attachment of the wet electrodes 302 to skin, the headband 202 is used to strap the wet electrodes 302 around one's head. The wet electrodes 302 may have a differential pair of electrodes or any number of electrodes being placed in variable distance from each other, as long as the distance is suitable for measuring EEG signals.

In the illustrative embodiment depicted in FIG. 3, the adapter 304 is used to ensure that the same processing component 110 can process sleep sensor data collected from either types of electrodes (i.e., to work with both the dry electrodes 202 and the wet electrodes 302, even if they have different electrodes placement or arrangement). To that end, the adapter includes mechanical fasteners on both its rear-facing and front facing surfaces. The rear-facing surface of the adapter includes female portions of mechanical fasteners corresponding to male portions extending from the front-facing surface of the wet electrodes. The front-facing surface of the adapter includes male portions of mechanical fasteners positioned to snap into the female portions of the mechanical fasteners built into the rear surface of the processing component 110. The adapter 304 includes conducting material, such as thin wires or bus lines, connecting the female fastener portions on its rear side to the male fastener portions on its front side. Preferably, all of the mechanical fasteners are conductive and made of a material suitable for conducting EEG signals without introducing and undesirable amount or noise or overly attenuating the signals.

Providing a user with the flexibility to select the desired wearing mode is advantageous. For example, while wet electrodes provide more accurate EEG recordings than dry electrodes and are more likely to stay on, dry electrodes are reusable and some users find them to be more comfortable to wear. Thus, a user may wish to use the dry electrodes on some nights. However, on other nights, the user may decide to use an eye mask, which may conflict with the use of the headband for the dry electrodes. Thus, the user might prefer a wet electrode system that simply attaches itself to the user either on the forehead or other parts of the user's head or elsewhere where the wet electrodes can detect an EEG signal.

Figure 4:
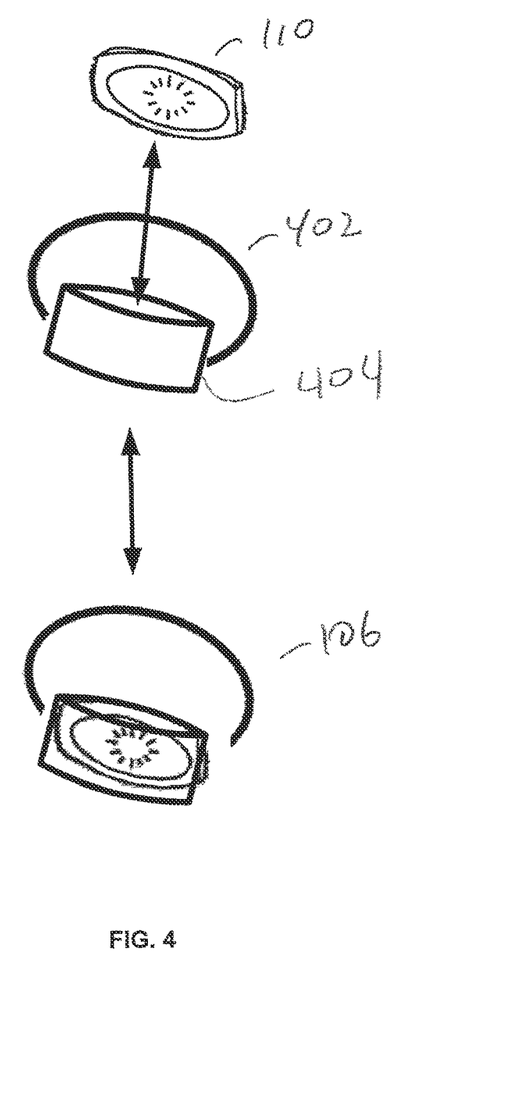
FIG. 4 depicts the multi-modal sleep system of FIG. 1 operating in a third mode of operation, according to an illustrative embodiment of the invention.

FIG. 4 depicts the multi-modal sleep system 100 of FIG. 1 operating in the third mode of operation 106, according to an illustrative embodiment of the invention. In this mode of operation, the system 100 only requires use of the processing component 110 and a wristband 402. The wristband 402 includes a pouch 404 for housing the processing component 110. In an alternative implementation, the wristband 402 includes male mechanical fastener portions for snapping into female mechanical fastener portions built into the rear surface of the processing component 110. The male mechanical fastener portions can, but need not, be conductive, as they are merely included for securely holding the processing component 110 in place.

As indicated above, in alternative embodiments, the processing component may take galvanic skin response at the user's wrist into account in its sleep stage processing. In such embodiments, suitable electrodes can be built into the wristband 402 and the male mechanical fastener portions would be constructed of or coated with a conductive material to convey the detected signals to the processing component 110 for analysis. In alternative embodiments of the processing component 110 that include a LED/photodiode pair, a photoplethysmographic signal may be generated by illuminating and measuring the light reflected from the wrist. This signal can then be processed to determine heart rate, heart rate variability and/or respiration rate, one or more of which is incorporated into the sleep staging algorithm.

In accelerometer only mode of operation depicted in FIG. 4, the system 100 utilizes a built-in accelerometer of the processing component 110 for measuring the physical movements of a user while asleep. In some embodiments, the user wears the wristband 402 with the processing component 110 around his/her wrist. In other embodiments, the wristband 402 is adjustable so that the user can wear the processing components 110 on or around any parts of his/her body, such as the ankle, legs, neck, waste, and arms. In certain embodiments, the movements of a user while asleep can also be detected by placing the processing components 110 in or under one's pillow or on other parts of one's bed.

In some implementations, the processing component 110 comprises a 3-axis (or triaxial) accelerometer capable of measuring the x-y-z angle tilts relative to the gravity vector. In other embodiments, the processing component 110 comprises one or more single or dual-axial accelerometers, instead of a single triaxial accelerometer. For example, an x/y-axis accelerometer may be used with a z-axis accelerometer.

In operation, as a user wearing the processing component 110 having the accelerometer moves, forces are exerted on a crystal in the accelerometer by a free-floating mass. Three crystals are needed to detect any force exerted by the free-floating mass in all three directions (x-y-z). Based on the exerted force, which is a vector with direction and magnitude, information about the direction and magnitude of a user's physical movement can be directly inferred to generate movement data. In some implementations, the hysteresis of an accelerometer is factored into the calculation of the movement data. With the movement data, the processing component 110 can track the physical movements of a user while asleep, such as tossing and turning. Based on the movement data, the processing component 110 can determine whether the user is awake or asleep, which may be indicated by the amount of detected movement exceeding a pre-determined threshold amount. Various types of algorithms may be used to process movement data collected by an accelerometer, such as the algorithms identified in "Comparing Different Methodologies Used in Wrist Actigraphy", by Stephen W. and Jennifer R. Spiro, Sleep Review, Summer 2001, available at http://www.sleepreviewmag.com/issues/articles/2001-07_04.asp. The movement data is then processed and plotted in a user-friendly and readable format to a user on an interface device, such as the base station 120 or mobile device 122 as described above. Quality of sleep may also be estimated based on the movement data. In some embodiments, the movement data may be tracked and stored so that an animation of the physical movements experienced by a user is depicted to the user.

In one particular embodiment, the movement data is analyzed to determine an activity value for a series of pre-determined time periods, such as every 30 seconds, to determine the extent of the user's movement moved during the pre-determined time period. Preferably, the time periods range from approximately 2 seconds up to about 1 minute. Preferably, the movement period is synchronized with a sleep stage analysis period. The activity value moved may be inferred from or indicated by the change in the movement vector as determined by the built-in accelerometer. For example, the processing component may sample the movement data at various sampling rates, such as 50 Hz, depending on the sensitivity of the built-in accelerometer (e.g., higher sensitivity may require a lower sampling rate). Each directional component of a movement vector (e.g., x component, y component, and z component) at a sampled time period is digitally filtered with a filter having pre-determined filter lengths (i.e., number of samples included in the filter) and coefficients. Test data may be gathered to experimentally determine optimal filter coefficients and filter lengths for each vector component of a movement vector based on the specific accelerometer used. Suitable filters include bandpass filters having frequency ranges from less than 1.0 Hz (e.g., 0.5 or 0.025 Hz) up to about 10 or 11 Hz. In some embodiments, the activity value during a pre-determined time period is determined based on an integration of magnitudes of filtered movement vectors with respect to time. In other embodiments, activity values are derived based on a number of zero-crossings in the accelerometer data. In still another embodiment, the activity value is based on an amount of time that the accelerometer output exceeds a threshold value. The activity value for a specified period of time is then compared to a threshold value. In the case that an activity value for a time period exceeds the threshold value, the user is determined to have made substantial movement during that period. The threshold value may be gathered from experimental test data and may differ depending on the gender, age, historical sleep data, or other type of user information. Various additional processing techniques can be applied to the activity value determination process. For example, movement data collected from adjacent time periods (e.g., from 0 to 30 seconds and 31-60 seconds) may be processed collectively to smooth out the transition point between two adjacent time periods or time windows (e.g., between 30 second and 31 second).

In some embodiments in which the user is wearing the processing component in a predetermined orientation (e.g., attached to the headband on the user's forehead), the processing component 110 has an algorithm that determines whether a user is in a vertical position, such as sitting down or standing up. This may be determined based on the magnitude of the accelerometer output associated with the longitudinal axis of the body. If the user is lying down, the accelerometer should detect little acceleration in this direction. If the user is vertical, the accelerometer output will reflect the force of gravity, being sitting or standing. If the processing component detects a vertical user orientation, the processing component 110 either determines that the user is awake or introduces a strong presumption that the user is awake—strong EEG data to the contrary may suggest sleep walking. As described above, this can be accomplished by using the vertical user determination as an input to the sleep stage determination algorithm, thereby heavily weighting the algorithm towards outputting a sleep stage of "awake".

In alternative embodiments, the processing component is configured to identify occurrences of a user sleeping in various positions. For example, accelerometer data can be analyzed to determine if the user is sleeping on their back versus their side or stomach by determining the orientation and/or movement of their head.

Figure 5:
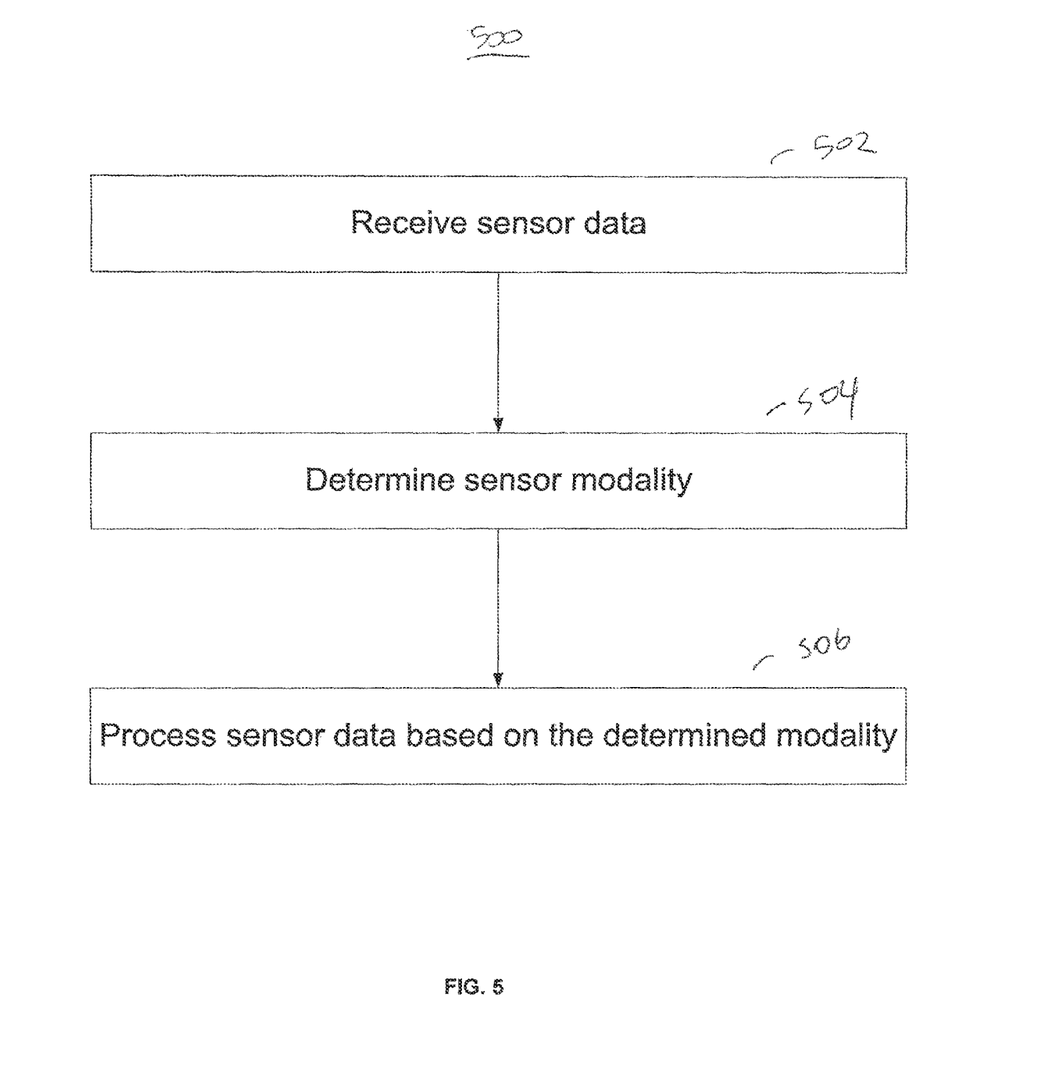
FIG. 5 is a flow chart of a method of determining a mode of operation of the multi-modal sleep system, according to an illustrative embodiment of the invention.

FIG. 5 is a flow chart of a method 500 of determining a mode of operation of the multi-modal sleep system, according to an illustrative embodiment of the invention. The method 500 begins with receiving sensor data (step 502) by the dry electrodes 202, wet electrodes 302, and/or an accelerometer. With the received sensor data, including EEG and/or movement data, the processing component 110 first determines sensor modalities before it begins analyzing the sensor data to extract sleep information from the data (step 504). In one embodiment, the processing component 110 makes such a determination based on a user indication of the mode of operation. In one such embodiment, the processing component 110 is built to include one or more buttons, switches, or other simple mechanical user input mechanisms for allowing a user to indicate whether the user is going to use only the accelerometer in the processing component 110, wet electrodes, or dry electrodes, or a combination of one or more types of sleep sensors. In another embodiment, a user may indicate the selected modality for the sleep session using a software application or other user interface element on the base station 120 or mobile device 122.

In an alternative embodiment, the processing component 110 makes a modality determination without any user input. For example, the processing component 110 measures the impedance of the signal received at the mechanical fasteners built into the processing component 110. In one embodiment, the processing component 110 stores a single impedance threshold value. If the input impedance 110 exceeds the threshold, for example a threshold value representative of infinite impedance, the processing 110 component determines that it is not connected to any electrodes, and thus operates solely using accelerometer data. If the processing component 110 detects a lower impedance, the processing component 110 determines that electrodes are connected and processes data obtained via the electrodes as well output by the accelerometer. In this embodiment, no distinction is made between data output by wet electrodes versus dry electrodes.

In other embodiments, the processing component 110 stores multiple impedance values, one corresponding to each sensor type that might be coupled to the processing component 110, and one value representing an infinite impedance. In this embodiment, the processing component 110 processing received sensor data differently depending on the specific type of sensor detected. For example, the processing component 110 may store one or more configuration parameters associated with each impedance value which is then used to process the received sensor data. Alternatively, the processing component 110 executes different processing algorithms based on the type of sensor detected.

In some embodiments, the processing component 110 includes additional sensing circuitry for sending test signals to electrodes to obtain a read-out of the input impedance. For example, a small electrical pulse may be generated and sent to the skin of a user via one electrode and measured at a second electrode. The measurement is then used to calculate input impedance of the skin according to Ohm's law.

Noise in an input signal is another parameter that may be used to determine sensor modality. Wet electrodes are less susceptible to noise than dry electrodes. The processing component 110 determines the noise levels in the signal or the Signal to Noise Ratio (SNR) of the signal and compares both the noise frequency (such as the 60 Hz power line noise) and amplitude with pre-stored threshold values to determine whether the user is wearing the dry or wet electrodes.

Testing data may be gathered on the usage of wet electrodes and dry electrodes to create signal profiles for both electrodes. A signal profile contains information idiosyncratic to a particular type of electrode and may be stored in the memory of the processing component 110. With the stored signal profile, the processing component 110 first generates a signal profile of an input signal and then compares the generated signal profile with the stored signal profiles to determine which one of the two types of electrodes is currently being used by the user. In some embodiments, signal profiles of different sleep stages may be experimentally collected and compared to actual signal profiles generated for the EEG signals detected while a user is asleep. The comparison between the signal profiles of different sleep stages and the actual EEG signal profile of a user enables the processing component 110 to better process the received input signal to more precisely determine sleep states, such as sleep stages that a user may have experienced and any duration associated therewith.

Once the sensor modality is determined, the processing component 110 invokes the appropriate processing method or algorithm for processing the received input signal at step 506 (i.e., an EEG signal, movement data, or a combination of both). Each type of sleep sensor or each combination of sleep sensors, such as wet electrodes, dry electrodes, or an accelerometer, may be associated with its particular processing method or algorithm dedicated to the analysis of data collected by the sleep sensor(s).

The foregoing embodiments are merely examples of various configurations of components of dry electrode systems described and disclosed herein and are not to be understood as limiting in any way. Additional configurations can be readily deduced from the foregoing, including combinations thereof, and such configurations and continuations are included within the scope of the invention. Variations, modifications, and other implementations of what is described may be employed without departing from the spirit and the scope of the invention. More specifically, any of the method, system and device features described above or incorporated by reference may be combined with any other suitable method, system, or device features disclosed herein or incorporated by reference, and is within the scope of the contemplated inventions.

What is claimed is:

1. A multi-modal sleep monitoring system, comprising:
a set of external sensors configured to measure physiological and environmental parameters;
a data processor configured to operate in a plurality of operating modes, the data processor configured to:
detect at least one sensor providing data to the data processor;
determine a sensor type associated with each of the at least one sensor;
determine a signal quality associated with each of the at least one sensor;
select a mode of operation based on the determined sensor type and signal quality of the detected at least one sensor;
receive data from the at least one detected sensor;
process the received data according to the selected mode of operation to output a characterization of a user's sleep; and
provide an output to the user which reflects sleep characterization from multiple nights.

2. The system of claim 1, wherein a first of the plurality of operating modes is selected in response to determining that the at least one detected sensor includes a first sensor type or combination of sensor types and a second of the plurality of operating modes is selected in response to determining that the at least one detected sensor includes a second sensor type or combination of sensor types, and wherein the data processor is configured to select the first of the plurality of operating modes in response to detecting a single sensor including an accelerometer, and the data processor is configured to select the second of the plurality of operating modes in response to detecting a single sensor including an EEG electrode.

3. The system of claim 1, wherein a first of the plurality of operating modes is selected in response to determining that the at least one detected sensor includes a first sensor type or combination of sensor types and a second of the plurality of operating modes is selected in response to determining that the at least one detected sensor includes a second sensor type or combination of sensor types, and wherein the data processor is configured to select the first of the plurality of operating modes in response to the data processor detecting a single sensor including an accelerometer, and the data processor is configured to select the second of the plurality of operating modes in response to the data processor detecting at least two sensors including an accelerometer and at least a sensor of a second sensor type.

4. The system of claim 3, wherein the second sensor type comprises a wet EEG electrode or a dry EEG electrode.

5. The system of claim 3, wherein the second of the plurality of operating modes comprises an operating mode that collectively processes data output by the accelerometer and the at least one sensor of a second sensor type.

6. The system of claim 3, wherein the second of the plurality of operating modes processes data output by the accelerometer to weight a sleep condition analysis otherwise executed on data output by the sensor of the second type.

7. The system of claim 1, wherein the data processor is configured to select the first of the plurality of operating modes in response to the data processor detecting a sensor including a dry EEG electrode, and the data processor is configured to select the second of the plurality of operating modes in response to the data processor detecting a sensor including a wet EEG electrode.

8. The system of claim 1, wherein the data processor includes a built-in accelerometer.

9. The system of claim 8, wherein the characterization of the user's sleep output by the data processor indicates whether the user is awake or asleep based on data output by the accelerometer.

10. The system of claim 1, comprising a removable adapter for coupling the data processor to a sensor of a first type.

11. The system of claim 10, wherein the data processor is configured to couple directly to a sensor of a second type without the adapter.

12. The system of claim 1, comprising a remote computing device configured for wireless communication with the data processor for receiving data indicative of the output sleep characterization.

13. The system of claim 1, wherein the remote computing device is further configured for presenting sleep characterization data based on the data received from the data processor.

14. A method for operating a multi-modal sleep monitoring system in a plurality of modes, comprising:
a set of external sensors configured to measure physiological and environmental parameters;
detecting by a data processor at least one sensor providing data to the data processor;
determining by the data processor a sensor type associated with each of the at least one sensor;
determining by the data processor a signal quality associated with each of the at least one sensor;
selecting by the data processor a mode of operation based on the determined sensor type and signal quality of the detected at least one sensor and of each of the at least one sensor;
receiving by the data processor data from the at least one detected sensor;
processing by the data processor the received data according to the selected mode of operation to output a characterization of a user's sleep; and
providing by the data processor an output to the user which reflects sleep characterization from multiple nights.

15. The method of claim 14, wherein a first of the plurality of operating modes is selected in response to determining that the at least one detected sensor includes a first sensor type or combination of sensor types and a second of the plurality of operating modes is selected in response to determining that the at least one detected sensor includes a second sensor type or combination of sensor types; and further comprising selecting by the data processor the first of the plurality of operating modes in response to detecting a single sensor including an accelerometer, and selecting by the data processor the second of the plurality of operating modes in response to the detecting a single sensor including an EEG electrode.

16. The method of claim 14, wherein a first of the plurality of operating modes is selected in response to determining that the at least one detected sensor includes a first sensor type or combination of sensor types and a second of the plurality of operating modes is selected in response to determining that the at least one detected sensor includes a second sensor type or combination of sensor types; and further comprising selecting, by the data processor, the first of the plurality of operating modes in response to the data processor detecting a single sensor including an accelerometer, and selecting, by the data processor, the second of the plurality of operating modes in response to the data processor detecting at lest two sensors including an accelerometer and at least a sensor of a second sensor type.

17. The method of claim 16, wherein the second sensor type comprises a wet EEG electrode or a dry EEG electrode.

18. The method of claim 16, wherein the second of the plurality of operating modes comprises an operating mode that collectively processes data output by the accelerometer and the at least one sensor of a second sensor type.

19. The method of claim 16, wherein operating in the second of the plurality of operating modes comprises processing data output by the accelerometer to weight a sleep condition analysis otherwise executed on data output by the sensor of the second type.

20. The method of claim 14, further comprising selecting the first of the plurality of operating modes in response to the data processor detecting a sensor including a dry EEG electrode, and selecting the second of the plurality of operating modes in response to the data processor detecting a sensor including a wet EEG electrode.

21. The method of claim 14, wherein the data processor includes a built-in accelerometer.

22. The method of claim 21, wherein the characterization of the users sleep output by the data processor indicates whether the user is awake or asleep based on data output by the accelerometer.

23. The method of claim 14, further comprising coupling, by a removable adapter, the data processor to a sensor of a first type.

24. The method of claim 23, further comprising coupling the data processor directly to a sensor of a second type without the adapter.

25. The method of claim 14, further comprising communicating with the data processor, via a remote computing device, for receiving data indicative of the output sleep characterization.

26. The method of claim 25, further comprising, by the remote computing device, presenting sleep characterization data based on the data received from the data processor.

\* \* \* \* \*